United States Patent
Black et al.

(10) Patent No.: US 9,358,377 B2
(45) Date of Patent: Jun. 7, 2016

(54) BRACHYTHERAPY DEVICES AND RELATED METHODS AND COMPUTER PROGRAM PRODUCTS

(75) Inventors: Robert D. Black, Chapel Hill, NC (US); Jeffrey C. Leung, Raleigh, NC (US)

(73) Assignee: Civatech Onocology, Durham, NC (US)

( * ) Notice: Subject to any disclaimer, the term of this patent is extended or adjusted under 35 U.S.C. 154(b) by 1217 days.

(21) Appl. No.: 12/728,584

(22) Filed: Mar. 22, 2010

(65) Prior Publication Data
US 2010/0233352 A1  Sep. 16, 2010

Related U.S. Application Data

(62) Division of application No. 11/846,075, filed on Aug. 28, 2007, now Pat. No. 7,686,756.

(60) Provisional application No. 60/823,814, filed on Aug. 29, 2006, provisional application No. 60/847,458, filed on Sep. 27, 2006, provisional application No. 60/926,349, filed on Apr. 26, 2007.

(51) Int. Cl.
*B05D 7/00* (2006.01)
*A61M 37/00* (2006.01)
*A61N 5/10* (2006.01)

(52) U.S. Cl.
CPC ......... *A61M 37/0069* (2013.01); *A61N 5/1027* (2013.01); *A61N 2005/1023* (2013.01)

(58) Field of Classification Search
CPC ............ A61M 37/0069; A61N 5/1027; A61N 2005/1023
USPC .................................. 600/1–8; 128/897, 898
See application file for complete search history.

(56) References Cited

U.S. PATENT DOCUMENTS

| | | | |
|---|---|---|---|
| 2,475,155 | A | 7/1949 | Rosenblatt |
| 3,351,049 | A | 11/1967 | Lawrence |

(Continued)

FOREIGN PATENT DOCUMENTS

| | | |
|---|---|---|
| DE | 19754870 A1 | 8/1998 |
| DE | 19953637 A1 | 5/2001 |

(Continued)

OTHER PUBLICATIONS

Albiero et a. "Short- and Intermediate- Term Results of $^{32}$P Radioactive β-Emitting Stent Implantation in Patients With Coronary Artery Disease; The Milan Dose-Response Study" *Circulation* 101(1):18-26 (2000).

(Continued)

*Primary Examiner* — Samuel Gilbert
(74) *Attorney, Agent, or Firm* — Myers Bigel & Sibley, PA

(57) ABSTRACT

A low-dose-rate (LDR) brachytherapy device having a spatiotemporal radiation profile includes an elongated body having a radioactive material in a spatial pattern to provide a spatial radiation profile with a radiation intensity that varies along a length of the elongated body. The radioactive material includes at least first and second radioisotopes having at least first and second respective decay profiles that together provide a temporal radiation profile that is different from the first and second decay profiles. The spatial radiation profile and the temporal radiation profile form a net spatiotemporal radiation profile configured to provide a radiotherapy plan for a patient.

22 Claims, 9 Drawing Sheets

(56) References Cited

U.S. PATENT DOCUMENTS

| | | | |
|---|---|---|---|
| 4,323,055 A | 4/1982 | Kubiatowicz | |
| 4,510,924 A * | 4/1985 | Gray | 424/1.61 |
| 4,702,228 A | 10/1987 | Russell, Jr. et al. | |
| 4,754,745 A | 7/1988 | Horowitz | |
| 4,763,642 A | 8/1988 | Horowitz | |
| 4,891,165 A | 1/1990 | Suthanthiran | |
| 5,079,333 A | 1/1992 | McGrath et al. | |
| 5,163,896 A | 11/1992 | Suthanthiran et al. | |
| 5,199,939 A | 4/1993 | Dake et al. | |
| 5,304,233 A | 4/1994 | Awadalia et al. | |
| 5,342,283 A | 8/1994 | Good | |
| 5,354,257 A | 10/1994 | Roubin et al. | |
| 5,405,309 A | 4/1995 | Carden, Jr. | |
| 5,407,528 A | 4/1995 | McGrath et al. | |
| 5,683,345 A | 11/1997 | Waksman et al. | |
| 5,691,442 A | 11/1997 | Unroe et al. | |
| 5,713,828 A | 2/1998 | Coniglione | |
| 5,782,740 A | 7/1998 | Schneiderman | |
| 5,840,009 A | 11/1998 | Fischell et al. | |
| 5,863,284 A | 1/1999 | Klein | |
| 5,869,140 A | 2/1999 | Blohowiak et al. | |
| 5,871,436 A | 2/1999 | Eury | |
| 5,873,811 A | 2/1999 | Wang et al. | |
| 5,894,133 A | 4/1999 | Armini | |
| 5,899,882 A | 5/1999 | Waksman et al. | |
| 5,916,143 A | 6/1999 | Apple et al. | |
| 5,993,374 A | 11/1999 | Kick | |
| 6,086,942 A | 7/2000 | Carden et al. | |
| 6,143,431 A | 11/2000 | Webster | |
| 6,149,889 A | 11/2000 | Chin et al. | |
| 6,152,869 A | 11/2000 | Park et al. | |
| 6,159,142 A | 12/2000 | Alt | |
| 6,248,057 B1 | 6/2001 | Mavity et al. | |
| 6,264,599 B1 | 7/2001 | Slater et al. | |
| 6,293,899 B1 | 9/2001 | Sioshansi et al. | |
| 6,358,531 B1 | 3/2002 | Day et al. | |
| 6,461,433 B1 * | 10/2002 | Carden et al. | 118/688 |
| 6,547,816 B1 | 4/2003 | O'Foghiudha | |
| 6,572,525 B1 | 6/2003 | Yoshizumi | |
| 6,575,888 B2 | 6/2003 | Zamora et al. | |
| 6,589,502 B1 | 7/2003 | Coniglione et al. | |
| 6,638,205 B1 | 10/2003 | Chan et al. | |
| 6,666,811 B1 | 12/2003 | Good | |
| 6,679,824 B1 | 1/2004 | Reed et al. | |
| 6,749,554 B1 | 6/2004 | Snow et al. | |
| 6,949,064 B2 | 9/2005 | Lowery et al. | |
| 7,118,729 B1 | 10/2006 | O'Foghiudha | |
| 7,762,940 B2 | 7/2010 | Henderson et al. | |
| 8,007,427 B2 | 8/2011 | Reed et al. | |
| 8,100,963 B2 * | 1/2012 | Roth et al. | 623/1.42 |
| 2002/0055851 A1 | 5/2002 | Jacobs et al. | |
| 2002/0164812 A1 | 11/2002 | DeLucas | |
| 2003/0084988 A1 | 5/2003 | Terwilliger et al. | |
| 2003/0092957 A1 | 5/2003 | Scott et al. | |
| 2003/0149329 A1 | 8/2003 | O'Foghludha | |
| 2004/0109823 A1 | 6/2004 | Kaplan | |
| 2006/0115424 A1 | 6/2006 | Gray | |
| 2007/0021643 A1 | 1/2007 | Lamoureux et al. | |
| 2007/0081940 A1 | 4/2007 | O'Foghludha | |
| 2008/0288068 A1 | 11/2008 | Kronowitz | |
| 2009/0131734 A1 | 5/2009 | Neustadter et al. | |
| 2012/0123189 A1 | 5/2012 | Ribbing et al. | |

FOREIGN PATENT DOCUMENTS

| | | |
|---|---|---|
| EP | 1008995 A1 | 6/2000 |
| FR | 2230374 | 12/1974 |
| WO | WO91/02766 A1 | 3/1991 |
| WO | WO97/19724 A1 | 6/1997 |
| WO | WO99/39765 A3 | 8/1999 |
| WO | WO00/29034 A1 | 5/2000 |
| WO | WO00/76557 A1 | 12/2000 |

OTHER PUBLICATIONS

Carter et al. "Current Status of Radioactive Stents for the Prevention of In-Stent Restenosis" *Int. J. Radiation Oncology Biol. Phys.* 41(1):127-133 (1998).

Cheng et al. "Neutron-Activatable Glass Seeds for Brachytherapy" *Journal of Nuclear Medicine* 35(5):242P (1994) Abstract Only.

Chettle et al. Techniques of in vivo neutron activation analysis'Phys. Med. Biol. 29(9):1011-1043 (1984).

Collé, R. "Chemical digestion and radionuclidic assay of TiNi-encapsulated 32P intravascular brachytherapy sources" *Applied Radiation and Isotopes* 50:811-833 (1999).

European Search Report for EP 03029892; Jun. 2, 2004.

Fischell et al. "The Beta-Particle-Emitting Radioisotope Stent (Isostent): Animal Studies and Planned Clinical Trials" *The American Journal of Cardiology* 78(3A):45-50 (1996).

Hausleiter et al. "A New Phosphorus-32 Balloon Catheter Device for Intracoronary Brachytherapy—Results from the Porcine Stent Model" *Journal of the American College of Cardiology* 35(2):51A (2000) Abstract Only.

Hetrick et al. "Antibacterial nitric oxide-releasing xerogels: Cell viability and parallel plate flow cell adhesion studies" *Biomatetials* 28:1948-1956 (2007).

Joensuu et al. "Physical and Biological targeting of Radiotherapy" *Acta Oncologica Suppl.* 13:75-83 (1999).

Lansky et al. "Patterns of Intimal Hyperplasia after $^{32}$P Brachytherapy: Results from the Prevent Randomized Clinical Trial" *Circulation* 100(18):1222-1223 (1999) Abstract only.

USPTO Office Action for U.S. Appl. No. 10/377,240; Jul. 11, 2007.

USPTO Office Action (Advisory Action) for U.S. Appl. No. 10/377,240; Feb. 13, 2007.

USPTO Office Action for U.S. Appl. No. 10/377,240; Aug. 15, 2006.

USPTO Office Action for U.S. Appl. No. 09/614,490; Oct. 31, 2003.

USPTO Office Action for U.S. Appl. No. 09/614,490; May 30, 2003.

USPTO Office Action (Advisory Action) for U.S. Appl. No. 09/614,490; Mar. 19, 2003.

USPTO Office Action for U.S. Appl. No. 09/614,490; Apr. 22, 2002.

USPTO Office Action (Advisory Action) for U.S. Appl. No. 09/506,611; Sep. 30, 2002.

USPTO Office Action for U.S. Appl. No. 09/506,611; Jul. 23, 2002.

USPTO Office Action for U.S. Appl. No. 09/506,611; Dec. 7, 2001.

Soloway et al. "The Chemistry of Neutron Capture Therapy" *Chem. Rev.* 98(4):1515-1562 (1998).

Nablo et al. "Poly(vinyl chloride-)Coated Sol-Gels for Studying the Effects of Nitric Oxide Release on Bacterial Adhesion" *Biomacromolecules* 5:2034-2041 (2004).

Wardeh et al. "β-Particle-Emitting Radioactive Stent Implantation—A Safety and Feasibility Study" *Circulation* 100(16):1684-1689(1999).

Yue et al. "Dosimetry Calculation for a Novel Phosphorus-32-Impregnated Balloon Angioplasty Catheter for Intravascular Brachytherapy" *Cardiovascular Radiation Medicine* 1(4):349-357 (1999).

Palladium hydroxide on Chemical Book. 2008 http://www.chemicalbook.com/ProductChemicalPropertiesCB3267682_EN.htm.

Instruction Manual, Micro4™, Controller for the Ultra Microsyringe Pump, World Precision Instruments, Inc., 2000.

Instruction Manual, UltraMicroPumpIII, UMP3 Microsyringe Injector and Micro4 Controller, World Precision Instruments, available prior to 2006.

\* cited by examiner

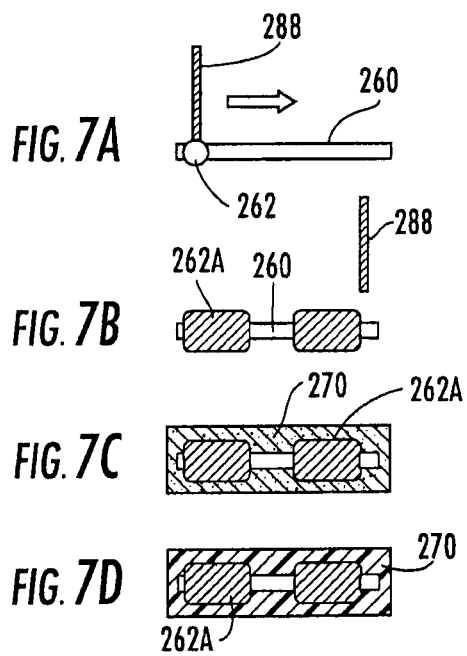
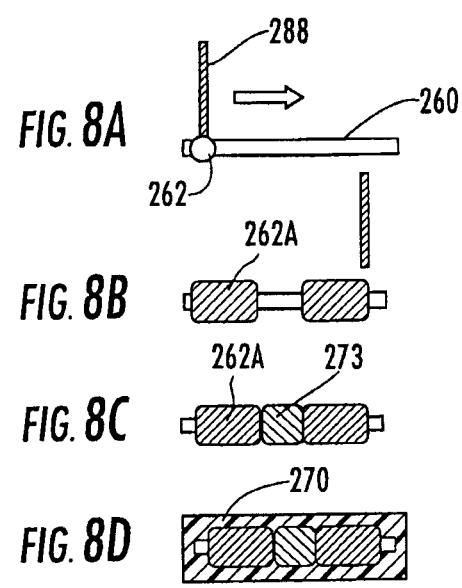

BRACHYTHERAPY DEVICES AND RELATED METHODS AND COMPUTER PROGRAM PRODUCTS

RELATED APPLICATIONS

This application is a divisional application of U.S. application Ser. No. 11/846,075, filed Aug. 28, 2007, now U.S. Pat. No. 7,686,756 which claims priority to U.S. Application Ser. Nos. 60/823,814, filed Aug. 29, 2006; 60/847,458, filed Sep. 27, 2006; and 60/926,349 filed Apr. 26, 2007, the disclosures of which are hereby incorporated by reference in their entireties.

FIELD OF THE INVENTION

The present invention relates to LDR brachytherapy radiation treatment methods, systems and computer program products.

BACKGROUND OF THE INVENTION

Roughly 230,000 new cases of prostate cancer are expected in the U.S. this year. Typically 80-90% of these cases are relatively early stage disease for which various treatment options are available. Primary treatment options involving radiation include external beam radiation therapy, which uses high-energy x-ray beams that intersect the prostate from multiple angles, and brachytherapy, in which a radioactive source is introduced into the prostate itself. Typical brachytherapy techniques use so-called "seeds," which are small (approximately 0.8×4.5 mm) cylinders that contain a radioactive element in a stainless-steel casing. A number of seeds, usually ranging from 80-120 seeds, are placed into the prostate using small gauge needles. The seeds can remain in place permanently while the emitted radiation decays over time. The common radioisotopes used in the seeds are iodine-125, palladium-103 and cesium-131. The goal of the radiation oncologist is to ensure that the total dose received by the cancer cells is sufficient to kill them. Seeds can be placed during an outpatient procedure in a single day and thus present an attractive treatment option for patients versus the many weeks required for external beam radiation therapy. Good candidates for brachytherapy seed therapy are typically patients having a PSA value≤10, a Gleason score of ≤7 and low-stage disease (T1c or T2a); however, patients with more advanced stage disease may also be treated with brachytherapy. In some cases, patients (e.g., with more advanced disease) may be candidates for brachytherapy plus external beam therapy. The use of seeds has grown rapidly, and long-term survival data for LDR brachytherapy treatment of the prostate is typically good.

In treating prostate cancer with brachytherapy seeds, it may be desirable to create a uniform radiation pattern within the prostate gland or within a region of the prostate gland. Computer code or treatment planning software can be used to select the number of seeds and their relative placement so that the desired radiation dose is achieved. This is a relative complex procedure because each individual seed is essentially a "point source" of radiation, and thus the radiation contributions from all of the seeds must be summed to achieve the total radiation dose. When the seeds are placed, great care is typically taken to ensure that they are arranged in the pattern specified by the treatment planning software. However, some deviation in seed placement may occur due to the divergence of needles as they are inserted. See Nath et al., Med Phys 27, 1058 (2000). A more problematic occurrence is the tendency of seeds to migrate once they exit the insertion needle [See Meigooni et al., Med Phys 31, 3095 (2004)]. It is not uncommon for seeds to migrate. In some cases, seeds may be caught in an efferent vessel and become embolized in the lung or excreted with urine. Gross movement of the seeds can create non-uniformities in the radiation pattern and thus potentially compromise the efficacy of therapy.

In an attempt to mitigate the post insertion migration of brachytherapy seeds, various products have been developed. For example, the RapidStrand™ device from Oncura (Arlington Heights, Ill., USA) is a hollow suture material that contains conventional seeds in a "linked sausage" arrangement. The suture material subsequently dissolves away leaving the seeds implanted in the patient. However, the seeds are held by the suture for a time that allows for healing and better retention of the seeds. Various so-called "sleeves for seeds" are also available. Another device that is commercially available from IBA (Louvain-la-Neuve, Belgium) under the trade name Radiocoil™ is a coiled structure device that contains rhodium metal that is proton-activated to produce Pd-103. Accordingly, the radioactivity is emitted along the entire length of the device.

Notably, the ability of the radiation oncologist to achieve the highest accuracy in therapy planning is hampered by the discrete nature of the current "seed" radiation sources due to their limited size and anisotropic radiation patterns. The tendency of seeds to move when placed in or near prostatic tissue is a problem that, while not invalidating this excellent form of therapy, creates a non-ideal situation for planning (e.g., requiring revalidation of the placement by CT scan). For example, migration of seeds to the lungs can result in incidental lung doses that are not favorable.

SUMMARY OF EMBODIMENTS ACCORDING TO THE INVENTION

According to embodiments of the present invention, methods of forming a low-dose-rate (LDR) brachytherapy device include providing a substrate having a micropattern thereon. The micropattern includes a plurality of spaced-apart wells. A radioactive material is deposited in at least some of the plurality of wells to provide a radiation profile.

According to further embodiments of the present invention, a low-dose-rate (LDR) brachytherapy device includes a substrate having a micropattern thereon. The micropattern includes a plurality of spaced-apart wells. A radioactive material is deposited in at least some of the wells.

According to some embodiments of the present invention, a low-dose-rate (LDR) brachytherapy device has a spatiotemporal radiation profile and includes an elongated body including a radioactive material in a spatial pattern to provide a predetermined spatial radiation profile with a radiation intensity that varies along a length of the elongated body. The radioactive material includes at least first and second radioisotopes having at least first and second respective decay profiles that together provide a temporal radiation profile that is different from the first or second decay profiles. The spatial radiation profile and the temporal radiation profile form a net spatiotemporal radiation profile configured to provide a radiotherapy plan of a patient.

According to some embodiments, a computer program product for controlling a radiation profile of a brachytherapy device having an elongated body is provided. The computer program product includes a computer readable medium having computer readable program code embodied therein. The computer readable program code includes computer readable program code that determines a net radiation profile having spatial and temporal components for at least one brachytherapy device having an elongated body. The net radiation profile is based on a radiation therapy plan for a patient. Computer readable program code is provided that controls the patterning of a radioactive material along a length of the elongated body of the at least one brachytherapy device in a spatial pattern to provide a spatial radiation profile with a radiation intensity that varies along the length of the elongated body. The radioactive material includes at least first and second radioisotopes having at least first and second respective decay profiles that together provide a temporal radiation profile that is different from the first and second decay profiles, and the spatial radiation profile and the temporal radiation profile form the net spatiotemporal radiation profile.

According to further embodiments of the present invention, a method of forming a LDR brachytherapy device includes determining a radiation profile for the brachytherapy device, and depositing a polymeric sol gel material in a pattern on the device. The polymeric sol gel material includes a molecularly dispersed radioisotope. The pattern includes a plurality of spaced-apart, discrete globules, each globule having a respective volume of the polymeric sol-gel material.

According to further embodiments of the present invention, a brachytherapy device includes an elongated substrate and a polymeric sol gel material having a molecularly dispersed radioisotope. The polymeric sol gel is deposited on the substrate in a pattern. The pattern includes a plurality of spaced-apart, discrete globules, each globule having a respective volume of the polymeric sol-gel material.

BRIEF DESCRIPTION OF THE DRAWINGS

FIG. 7A-7D is a schematic diagram of devices and methods in which a radioactive material is deposited on a fiber according to embodiments of the present invention;

FIG. 8A-8D is a schematic diagram of devices and methods in which a radioactive material and a radio-opaque material is deposited on a fiber according to embodiments of the present invention;

Figure 1A:
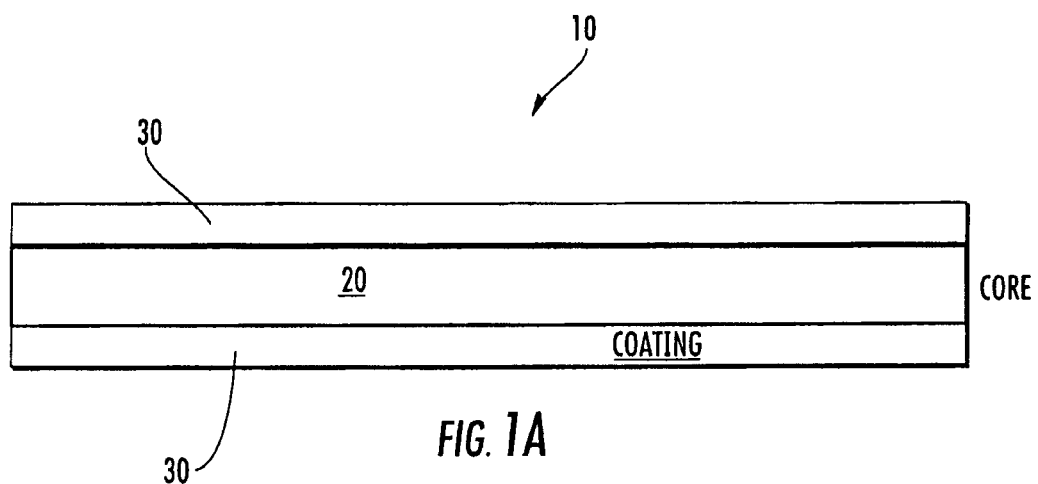
FIGS. 1A-1E are schematic diagrams of brachytherapy devices according to embodiments of the present invention.

DETAILED DESCRIPTION OF EMBODIMENTS
OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc, may be used herein to describe various elements, components, regions, layers and/or sections, these elements, components, regions, layers and/or sections should not be limited by these terms. These terms are only used to distinguish one element, component, region, layer or section from another region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

As used herein, the term "globule" refers to a discrete volume of material, such as a sol gel material. Globules of material can be deposited on a substrate or in a micro-well, for example, using a micro-syringe pump or micro-pipette according to embodiments of the present invention. In some embodiments, the volume of material in globule can be controlled, for example, with an accuracy of better than 10%. Typical sizes of globules are between 5 and 500 nanoliters.

According to some embodiments of the present invention, a low-dose radiation (LDR) brachytherapy device is provided. The device can include a micropattern of a radioactive or activatable material on a substrate. In some embodiments, the micropattern includes a plurality of spaced-apart wells on the substrate. A radioactive material (or an activatable material) can be deposited in at least some of the wells. The substrate can be an elongated strand, such as a suture.

In some embodiments, the radioactive material (or activatable material) is selectively deposited (e.g., in globules) in the wells to provide non-uniform and/or discontinuous radiation pattern.

According to further embodiments of the present invention, a plurality of globules of a radioactive or activatable material are deposited on a substrate such that the radioactive or activatable material forms a radiation profile. The substrate may include a micropattern, such as a well pattern for receiving the radioactive or activatable material therein or the substrate may be devoid of a pattern (e.g., the substrate may be essentially flat or smooth). Examples of suitable substrates include a suture, such as a monofilament suture, or other biodegradable or non-biodegradable material that is biocompatible and may be implanted in a patient, such as a glass fiber or a metal fiber. Biodegradable materials include, but are not limited to, polydioxanone, polylactide, polyglycolide, polycaprolactone, and copolymers thereof. Other copolymers with trimethylene carbonate can also be used. Examples are PDS II (polydioxanone), Maxon (copolymer of 67% glycolide and 33% trimethylene carbonate), and Monocryl (copolymer of 75% glycolide and 25% caprolactone). Non-biodegradable materials include nylon, polyethylene terephthalate (polyester), polypropylene, expanded polytetrafluoroethylene (ePTFE), glass and metal (e.g. stainless steel), metal alloys, or the like.

In some embodiments, a low-dose radiation (LDR) brachytherapy device is formed by determining a radiation profile for the device based on a patient radiation treatment plan and depositing a polymeric sol gel material on the device in a pattern. The polymeric sol gel material can include a molecularly dispersed radioisotope. The pattern can include a plurality of spaced-apart, discrete globules, each globules having a respective volume of the polymeric sol gel material.

In particular embodiments, the polymeric sol gel material can include two radioisotopes having respective decay profiles. Accordingly, the spatial pattern and the at least two different decay profiles can provide a spatiotemporal radiation profile that may be fabricated to implement a radiation therapy plan for an individual patient. For example, ratio of two or more isotopes can be modified to achieve a time-varying radiation profile and can be used to increase the radiobiological effectiveness of the LDR therapy. In some embodiments, different isotopes of the same element can be used.

In some embodiments, the output of conventional radiation therapy planning software or other suitable radiation therapy plans can be used to determine the spatial and/or temporal radiation profile for a device. The device can be fabricated using calculated amounts of radioactive material, such as a radioactive sol gel material, that may be dispersed in a spatial pattern along a length of an elongated LDR device and/or using a mixture of two or more isotopes to achieve an appropriate temporal profile.

The radiation therapy plan and spatial and/or temporal radiation profile of the device can take into account the effects of post-implantation edema, e.g., by adding extra length to the device and/or increasing the radioactivity of the proximal and distal ends of the device that may be implanted at an outer boundary of the tumor or organ. In particular embodiments, the device can include a filament that can extend outside the patient after implantation. The filament may have sufficient tensile strength to allow a physician to pull the brachytherapy device in the proximal direction to readjust the position of the device after placement. Once final positioning is achieved, the filament can be severed close to the skin surface.

In particular embodiments, computer program products can be used to determine a pattern of radioactive portions and non-radioactive portions of a device and/or mixture(s) of radioisotopes to create a spatial and/or temporal radiation profile when implanted in the patient and/or to control the fabrication of the brachytherapy device.

Brachytherapy devices may be provided that include a polymeric material having a chemically distributed therapeutic isotope throughout. The polymeric material may include a radioisotope, or in some embodiments, the polymeric material can have at least one nuclide that is activatable by exposure to radiation, such as by neutron or proton bombardment. As used herein, the term "activate" means to make radioactive, for example, by exposure to radiation. The nuclide or the radioisotope can be a chemically bound constituent of the polymer, or dispersed uniformly within the polymer matrix or chelated to certain substituents of the polymer without chemical bonding. The nuclide can be a transition metal. In particular embodiments, the brachytherapy device can include an elongated core comprising a polymeric sol-gel material including a polymer chain having at least one nuclide that is activatable by exposure to radiation. The nuclide can be a chemically bound constituent of the polymer chain and can be stoichiometrically distributed in the polymeric material, or dispersed substantially uniformly within the polymer matrix or chelated to certain substituents of the polymer without chemical bonding. In some embodiments, aspects of the manufacturing process used in creating a radioactive "string" or elongated core can be performed with "cold" material (non radioactive). Then, using an activation pathway, the cold precursor material is made "hot" (radioactive) closer to the time when the end user is ready to utilize the device for therapy.

In specific embodiments, sol-gel processing can be used to form radioactive or activatable materials, e.g., to form polymeric fibers of the requisite dimensions for use in LDR (low-dose-rate) brachytherapy. Exemplary sol gels are discussed herein. However, any suitable radioactive material, including radioactive materials or materials that may become radioactive through irradiation, may be used.

An example of a brachytherapy device 10 is shown in FIG. 1A. The device 10 includes an elongated polymer core 20 and a biocompatible coating 30. The device 10 is sized and configured for implantation into a patient, such as for implantation into the prostate. For example, the device 10 can be tube-shaped having a diameter of less than 1 mm or less than 0.8 mm. The polymer core 20 can be fabricated using the techniques described herein, including sol-gel fabrication techniques.

In particular embodiments, the polymer core 20 can be a biocompatible material such as surgical suture material and can have radioactive material deposited thereon. The coating 30 can be any suitable biocompatible coating and may be applied using techniques known to those of skill in the art, including dip-coating. The core 20 can be entirely radioactive, or portions of the core 20 can be radioactive. In some embodiments, the core 20 is non-radioactive, but can be irradiated after formation to activate at least one nuclide in the polymer to provide a radioactive device.

Figure 1B:
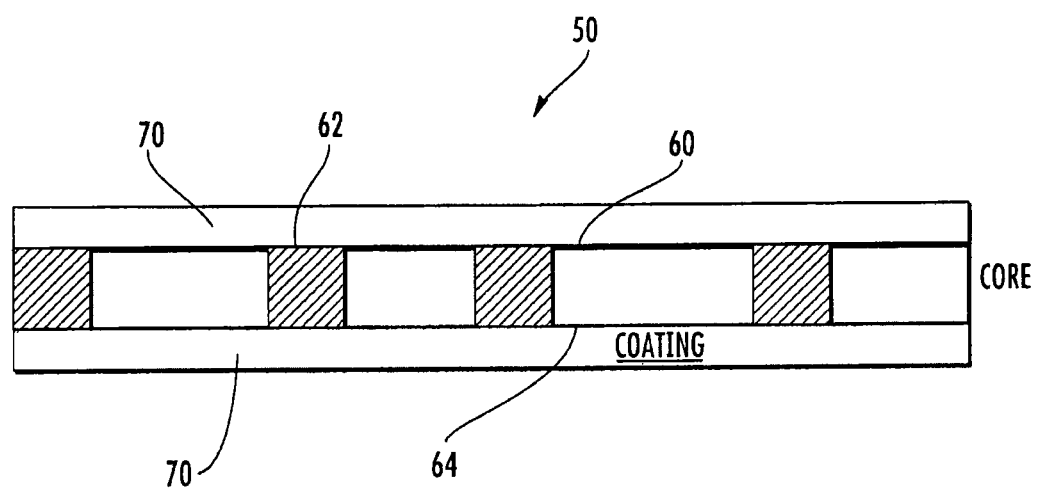

For example, as shown in FIG. 1B, a device 50 includes a polymer core 60 and an optional coating 70. The polymer core 60 includes radioactive portions 62 and non-radioactive portions 64. In some embodiments, the relative sizes of the radioactive portions 62 and the non-radioactive portions 64 can be configured for a particular treatment plan for an individual patient, such as based on the size and positioning of a tumor and the desired radiation pattern for treatment. Typically, a plurality of devices, such as the device 50, can be made such that each device is configured for a specific placement in the body, and so that, in position, the plurality of devices delivers a desired radiation pattern.

In some embodiments, relatively precise control over the radiation profile may be achieved by controlling the size and spacing of the radioactive portions 62 and nonradioactive portions 64. In particular embodiments, the radioactive portions 62 may be formed from densely deposited globules of sol gel material, such as at least 2 to 20 or more globules per 5 mm.

Figure 1C:
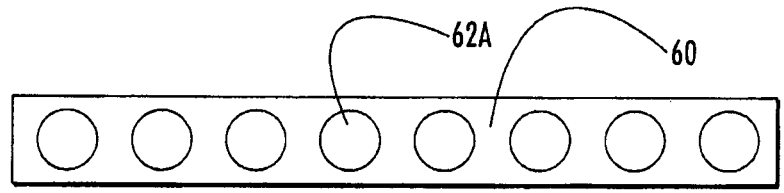
Figure 1D:
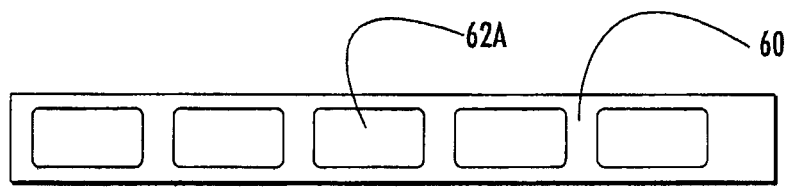
Figure 1E:
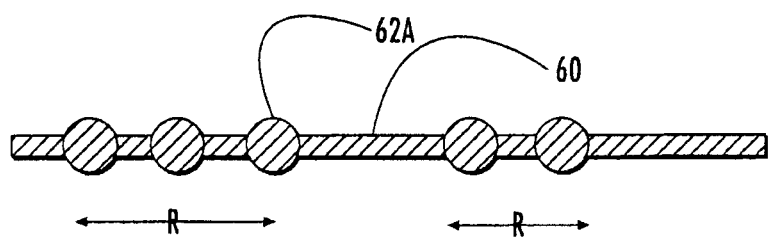

For example, as shown in FIGS. 1C-1E, globules 62A of radioactive material can be deposited on the core 60. The globules 62A can be densely deposited in radioactive regions "R" (e.g., in FIG. 1E). In some embodiments, the globules 62A can have a sufficient density so that the radioactive regions "R" have a radiation profile that is substantially the same or similar to a continuous line source (e.g., between 2 and 20 or more globules per 5 mm). However, it should be understood that any density of globules may be used. The globules 62A can be deposited on an unpatterned substrate (FIG. 1E) or on a substrate patterned with micro-wells that receive the droplet or globules 62A therein (FIGS. 1C-1D). The micro-wells can be any suitable shape, including round, rectangular, or square shapes.

In addition, the density and/or volume of the globules 62A can be controlled and/or calculated to provide radioactive regions "R" as shown in FIG. 1B that have different radiation intensities. The material(s) used to form the globules 62A can also include one or more radioisotopes of a predetermined mixture or two or more materials including different radio-isotopes to provide a desired decay profile for the radioactive regions "R."

With reference to FIGS. 1A-1E, it should be understood that the portions 64 are referred to herein as "non-radioactive" for ease of presentation; however, the portions 64 may emit a relatively small amount of radiation in comparison with the radioactive portions 62.

In particular embodiments, the core 60 is formed of suture material or other biocompatible material. For example, the radioactive portions 62 of FIG. 1B can be formed of a plurality of spaced-apart, discrete radioactive sol gel globules. The sol gel globules may be deposited in a pattern on the core 60 or other suitable substrate material. The sol gel material may then cured be, for example, at a temperature of less than 150° C., or less than 120° C., to form a radioactive or activatable xerogel. Two or more radioisotopes can be incorporated into the sol gel material to provide a desired decay profile. More than one sol gel material can be used, and each material can have different radioisotope(s) therein so that the decay profile can vary along the length of the core 60.

In certain embodiments, a pre-patterned substrate can be used. For example, as shown in FIGS. 1C-1D, a substrate 60 includes a plurality of micro-wells 62A with a radioactive material (such as radioactive sol gel) received therein. Any suitable micro patterning technique can be used to form the micro-wells 62A on the substrate 60, such as photolithographically defined wells, stamping, drilling, laser cutting or molding. The micro-wells 62A can each be filled with the radioactive material or the micro-wells 62A can be selectively filled or remain empty to provide a desired radiation profile pattern. In some embodiments, some of the micro-wells can be filed with radio-opaque material or other markers configured to increase the visibility of the device using medical imaging techniques, such as ultrasound, MRI, or other imaging techniques.

Figure 2A:
FIGS. 2A-2B are digital images of micropatterned substrates according to embodiments of the present invention.
Figure 2B:

FIGS. 2A-2B are digital images of micropatterned sutures (0.4 mm in diameter in this example) or substrates according to embodiments of the present invention. It should be understood that globules may be positioned in all or some of the wells therein. As illustrated in FIGS. 2A-B, the wells can be apertures that extend through the substrate material.

Figure 3:
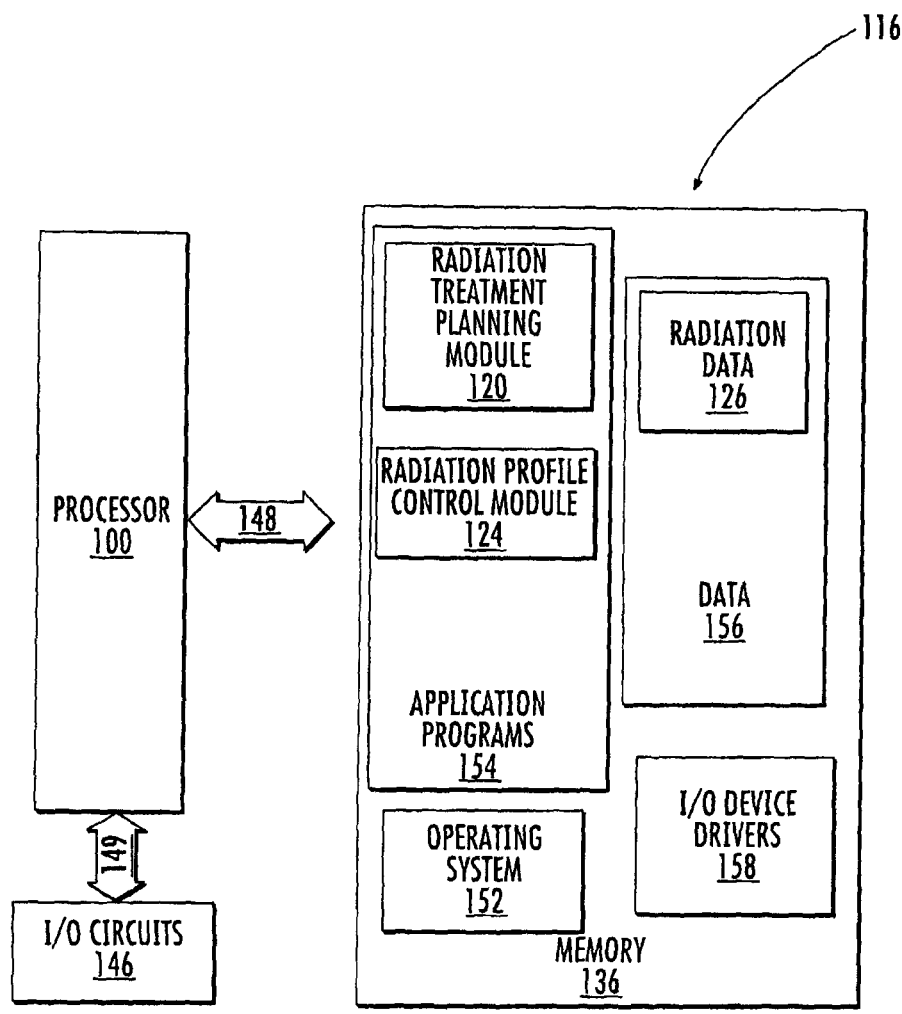
FIG. 3 is a block diagram illustrating methods, systems and computer program products according to embodiments of the present invention.

FIG. 3 illustrates an exemplary data processing system that may be included in devices operating in accordance with some embodiments of the present invention. As illustrated in FIG. 3, a data processing system 116, which can be used to carry out or direct operations includes a processor 100, a memory 136 and input/output circuits 146. The data processing system may be incorporated in a portable communication device and/or other components of a network, such as a server. The processor 100 communicates with the memory 136 via an address/data bus 148 and communicates with the input/output circuits 146 via an address/data bus 149. The input/output circuits 146 can be used to transfer information between the memory (memory and/or storage media) 136 and another component, such as a deposition controller, beam controller or irradiation device for selectively patterning a brachytherapy device with radiation or radioactive material. These components may be conventional components such as those used in many conventional data processing systems, which may be configured to operate as described herein.

In particular, the processor 100 can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 may be a content addressable memory (CAM).

As further illustrated in FIG. 3, the memory (and/or storage media) 136 may include several categories of software and data used in the data processing system: an operating system 152; application programs 154; input/output device circuits 146; and data 156. As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device circuits 146 typically include software routines accessed through the operating system 152 by the application program 154 to communicate with various devices. The application programs 154 are illustrative of the programs that implement the various features of the circuits and modules according to some embodiments of the present invention. Finally, the data 156 represents the static and dynamic data used by the application programs 154, the operating system 152 the input/output device circuits 146 and other software programs that may reside in the memory 136.

The data processing system 116 may include several modules, including a radiation treatment planning module 120, a radiation profile control module 124, and the like. The modules may be configured as a single module or additional modules otherwise configured to implement the operations described herein for planning a radiation treatment plan, determining a spatial and/or temporal radiation profile for a device and/or controlling the deposition of radioactive material or irradiating a device to form a desired radiation pattern. The data 156 can include radiation data 126, for example, that can be used by the radiation treatment planning module 120 and/or radiation profile control module to design and/or fabricate a brachytherapy device.

While the present invention is illustrated with reference to the radiation treatment planning module 120, the radiation profile control module 124 and the radiation data 126 in FIG. 3, as will be appreciated by those of skill in the art, other configurations fall within the scope of the present invention. For example, rather than being an application program 154, these circuits and modules may also be incorporated into the operating system 152 or other such logical division of the data processing system. Furthermore, while the radiation treatment planning module 120 and the radiation profile control module 124 in FIG. 3 is illustrated in a single data processing system, as will be appreciated by those of skill in the art, such functionality may be distributed across one or more data processing systems. Thus, the present invention should not be construed as limited to the configurations illustrated in FIG. 3, but may be provided by other arrangements and/or divisions of functions between data processing systems. For example, although FIG. 3 is illustrated as having various circuits and modules, one or more of these circuits or modules may be combined, or separated further, without departing from the scope of the present invention.

Figure 4A:
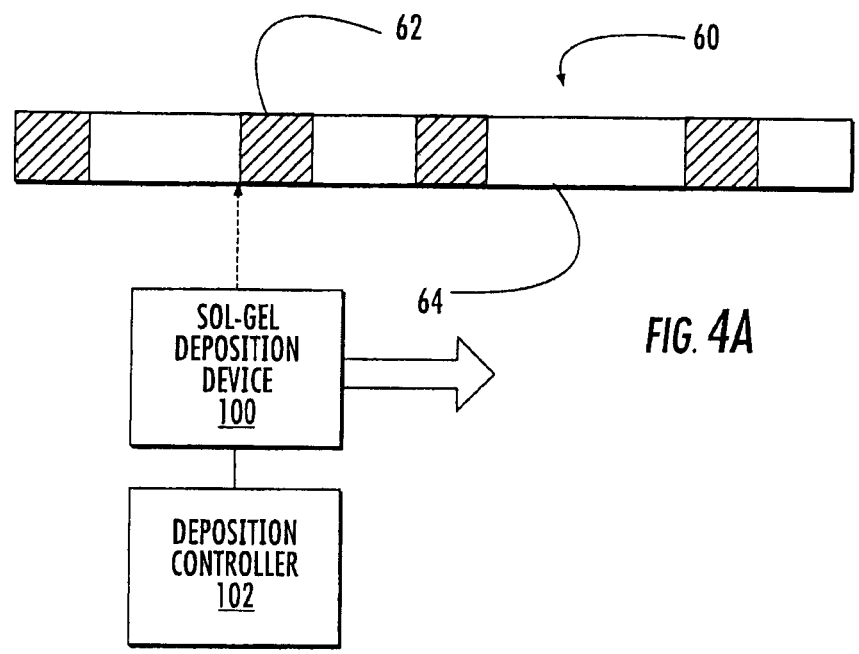
FIG. 4A is a schematic diagram illustrating a deposition configuration for selectively depositing a material on a brachytherapy device according to embodiments of the present invention.

As shown in FIG. 4A, a sol-gel deposition device 100 is controlled by a deposition controller 102 (e.g., via the I/O circuits 146 of FIG. 3) to form the radioactive portions 62 of the device 60. In particular, the sol gel material can be deposited in a plurality of spaced-apart, discrete globules. Each globule of sol gel material can include a particular volume of the material so that the pattern of sol gel globules provide a desired radioactive profile. The globules can have relatively precisely deposited volumes between 5 and 500 nanoliters or between 10 and 200 nanoliters. Two or more radioisotopes may be used to provide a desired decay profile, which may vary along a length of the device. In some embodiments, the volume of the sol gel material can be calculated by the radiation treatment planning module 120 and/or radiation profile control module 124 of FIG. 3. Without wishing to be bound by theory, the amount of radioactive material is generally directly related to the amount of radiation emitted. For example, twice the amount of a radioactive material will generally result in twice the amount of radiation being emitted. Accordingly, in some embodiments, precision deposition can be used to deposit desired amounts of radioactive material to achieve a particular radiation profile.

The sol gel deposition device 100 can be a micropipette, a microsyringe pump, or other suitable extrusion and/or deposition device, such as an Ultramicrosyringe II by World Precision Instruments, LTD, Stevenage, Hertfordshire, England. The deposition device 100 can deposit a volume of material with an accuracy of within 10% or less of the calculated volume.

The sol gel material can be formed using a radioactive precursor material so that it is radioactive at the time that it is deposited on the device 60 or, in some embodiments, the sol gel material can in an inactive form during deposition and can be irradiated (e.g., by neutron bombardment) after it is deposited and/or cured to provide a radioactive device.

Figure 4B:
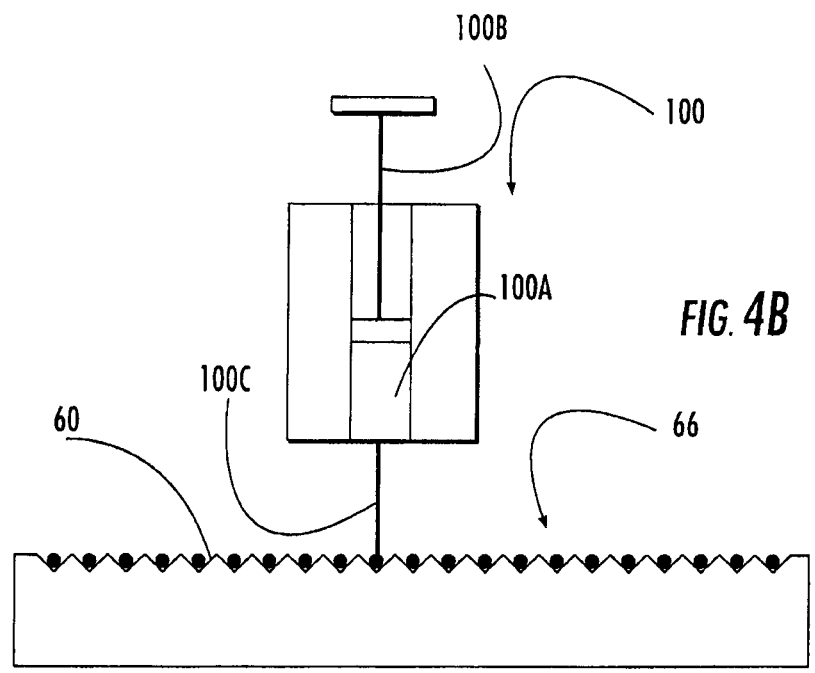
FIG. 4B is a schematic diagram illustrating a micro-syringe deposition system for use with a cartridge of substrates according to embodiments of the present invention.
Figure 4C:
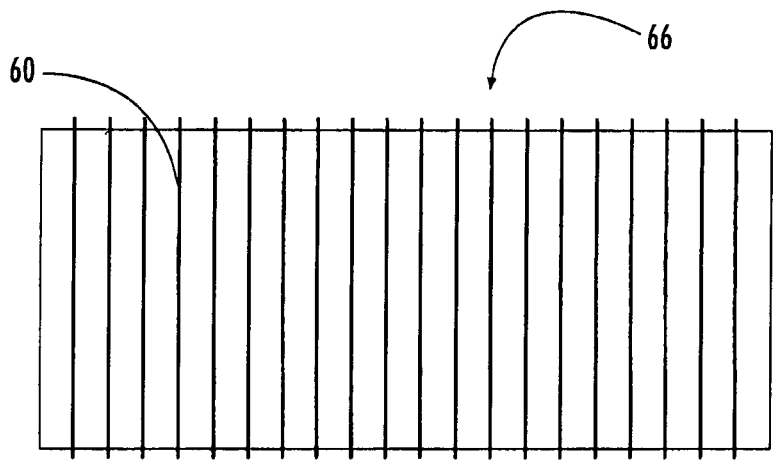
FIG. 4C is a top plan view of the substrate cassette of FIG. 4B.
Figure 4D:
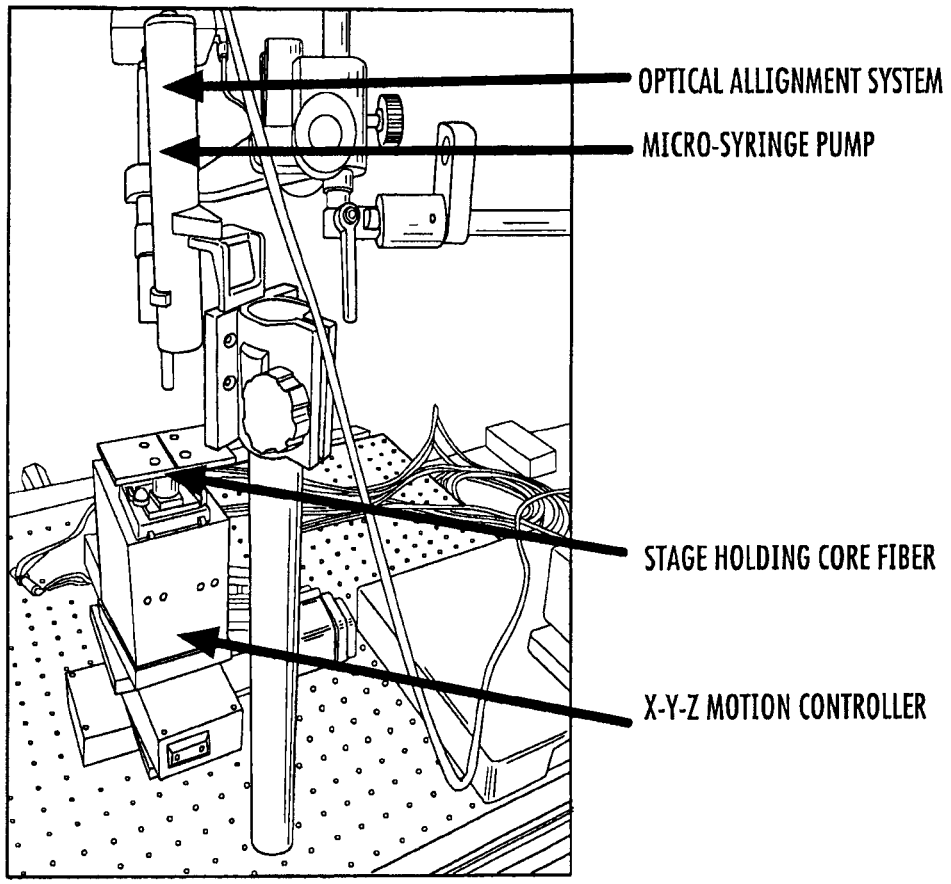
FIG. 4D is a digital image of a micro-syringe pump according to embodiments of the present invention.

In some embodiments, as shown in FIGS. 4B-4C, a plurality of substrates 60 can be positioned on a cassette 66. The cassette 66 includes grooves, and the substrates 60 are positioned in the grooves. The sol-gel deposition device 100 of FIG. 4A can be used to deposit radioactive or activatable material on the substrates. For example, as shown in FIG. 4B, the deposition device 100 is a micropipette having a reservoir 100A, a plunger 100B and a micropipette needle 100C. The plunger 100B pushes a desired amount of material, such as a radioactive sol gel, through the needle 100C and deposits globules of the material at desired positions on the substrates 60. The deposition controller 102 of FIG. 4A can include radiation treatment planning software for controlling the deposition device 100 to provide a desired radiation profile for the substrates 60 as part of a treatment plan. FIG. 4D is a digital image of a micro-syringe pump and X-Y-Z motion controller for depositing radioactive material on the substrates.

Figure 5:
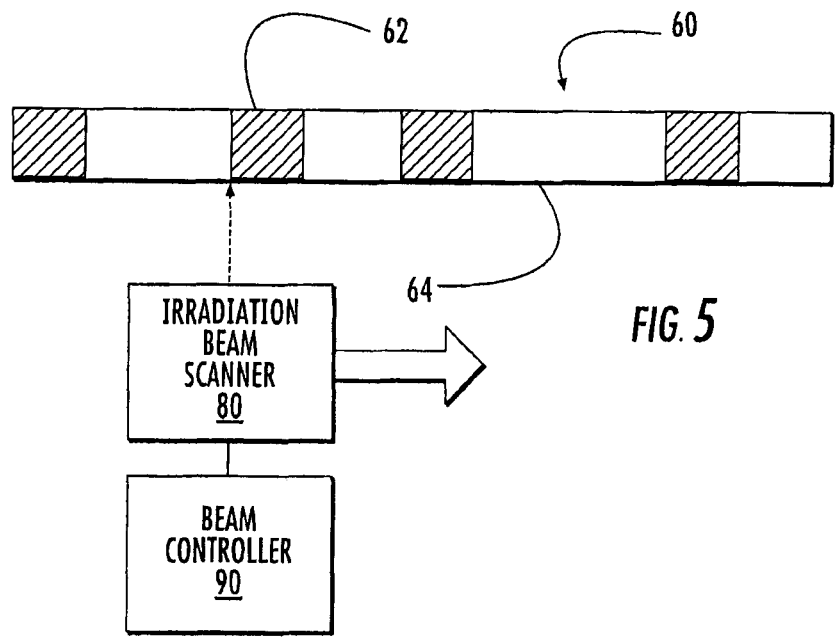
FIG. 5 is a schematic diagram illustrating a scanning device for selectively irradiating a brachytherapy device according to embodiments of the present invention.
Figure 6:
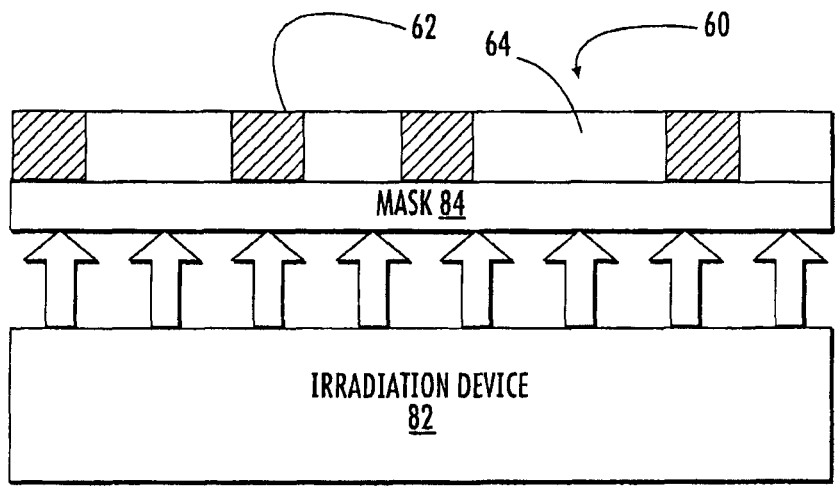
FIG. 6 is a schematic diagram illustrating a mask and radiation source configuration for selectively irradiating a brachytherapy device according to embodiments of the present invention.

Although embodiments of the present invention are described with respect to deposition techniques, it should be understood that other techniques can be used to provide a desired radiation pattern. For example, as shown in FIGS. 5-6, a non-radioactive polymer can be activated by radiation using various techniques to form the radioactive portions 62 and the non-radioactive portions 64 of the core 60. With reference to FIG. 5, an irradiation beam scanner 80 can be used to bombard the core 60 with radiation, such as from a focused proton or neutron beam. The beam controller 90 controls the relative position of the core 60 with respect to the beam scanner 80 to form the desired pattern of radioactive portions 62 and non-radioactive portions 64. For example, the beam scanner 80 can move horizontally with respect to the core 60 to raster scan the core 60 such that the portions 62 receive more radiation than the portions 64. The beam controller 60 can control the movement of the beam scanner 80 and/or the core 60 to create the desired pattern of radioactive and non-radioactive portions 62, 64, for example, by scanning relatively slowing on the portions 62 to activate the portions 62 and by scanning quickly over the portions 64 to reduce activation of the portions 64.

As shown in FIG. 6, the core 60 can be activated with an irradiation source 82 and a mask 84. The mask 84 selectively permits radiation from the source 82 to impinge upon the core 60 to form radioactive portions 62 and non-radioactive portions 64.

As shown in FIGS. 7A-7D, an extrusion device 288 (such as a micro-syringe) is used to deposit discrete globules 262 of sol gel material on a substrate 260. The sol gel is heated to form a xerogel and, in some cases, heated further to fuse with the substrate 260 (FIG. 7B) to provide radioactive portions 262A, which may be a backbone fiber, silica or suture material. A biocompatible polymer coating 270 can be applied over the substrate 260 (FIG. 7C) and can be textured to enhance its visibility in ultrasound imaging (FIG. 7D). Biocompatible polymer coatings include, but are not limited to, polyurethane, silicone, Teflon, parylene, polyethylene, and polyester (PET).

In FIGS. 8A-8B, a radio-isotope containing sol gel globule 262 is deposited on the substrate 260 in a radiation profile pattern. In FIG. 8C, radio-opaque material 273, such as a metallic paste, is deposited so that the material 273 can increase visibility in medical imaging techniques, such as ultrasound imaging. A biocompatible polymer coating 270 that is optionally textured is applied in FIG. 8D.

Figure 9A:
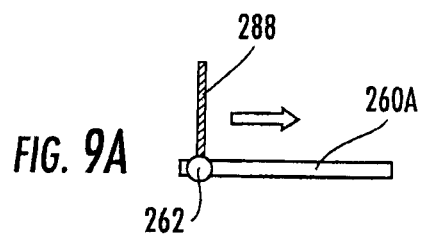
FIG. 9A-9D is a schematic diagram of devices and methods in which a radioactive material is deposited on a dual-rail backbone fiber according to embodiments of the present invention.
Figure 9B:
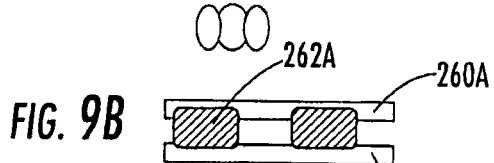
Figure 9C:
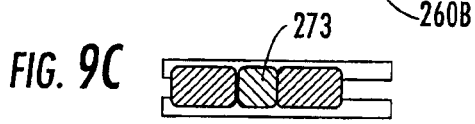
Figure 9D:
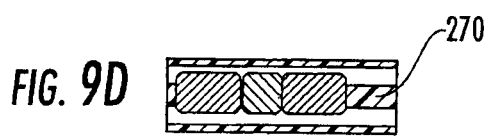

As shown in FIG. 9A, a sol gel globule 262 is deposited by the extrusion device 288 on the substrate 260A. A second substrate 260B is positioned adjacent the first substrate 260A in FIG. 9B to provide a "dual-rail" backbone fiber, e.g., to increase a surface region for depositing the globules 262. The cured sol gel material 262A can optionally be used with radio-opaque material 273 and/or a biocompatible coating 270 (FIGS. 9C and 9D).

Figure 10A:
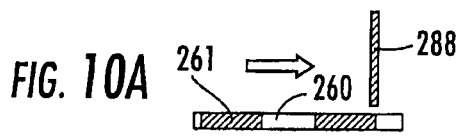
FIG. 10A-10D is a schematic diagram of devices and methods in which an adhesion promotion coating is used to promote adhesion between a radioactive material and the substrate according to embodiments of the present invention.
Figure 10B:
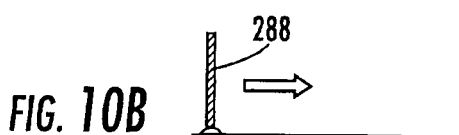
Figure 10C:
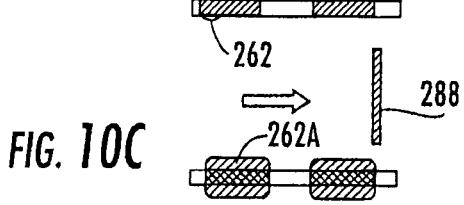
Figure 10D:

As shown in FIG. 10A, a coating layer 261 can be applied to the substrate 260 by a deposition device 280 to promote/increase adhesion and/or to limit the lateral spread of the sol gel material. The deposition device 280 may be the same or different from the deposition device 288 used to deposit the sol gel globules 262 as shown in FIG. 10B. The sol gel globules are deposited on the coating layer 261 in the desired pattern and cured (FIG. 10C). Optionally, a biocompatible and/or textured coating 270 can be applied (FIG. 10D).

Moreover, although the configurations of FIGS. 7A-7D, 8A-8D, 9A-9D, and 10A-10D are illustrated with respect to generally non-patterned substrates, it should be understood that the globules of radioactive materials and/or radio-opaque materials can be deposited in similar patterns on a micro-patterned substrate having wells for receiving the globules therein.

In particular embodiments, palladium-103 can be used in a sol gel material and/or encased in a common, biocompatible polymer. Devices according to embodiments of the present invention can be designed to work with existing brachytherapy insertion tools and protocols. Various materials can be used. For example, it may be desirable to design a core that can biodegrade once the radiation source has decayed. Lighter elements can be used so that there can be less self-shielding of the emitted radiation, which is a complication for metal-encased seeds. The device can be designed so that it can be cut to length easily at the user site. In some embodiments, the device can be placed through conventional needles using existing LDR brachytherapy tools. The devices described herein can be cut to length. The core can contain the activatable nuclide so that it is a stoichiometrically distributed (and possibly part of a chemical compound) precursor isotope. Processing of the core can proceed without radioactive materials. The core can be activated by energetic nucleons (protons or neutrons) to form a therapeutic radioisotope. A biocompatible outer coating that protects the core and optimizes the mechanical properties core (strength, flexibility) for a specific therapeutic application can be applied. The outer core can also be textured for increased ultrasound image appearance.

Sol Gel Formulations

Various radioactive or activatable materials can be used according to embodiments of the present invention. In particular embodiments, a sol gel solution was prepared from the following: a) a trifunctional alkyl silane such as isobutyltrimethoxysilane (BTMOS)

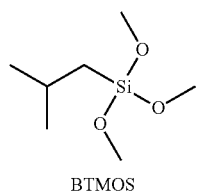

BTMOS and
b) a trifunctional aminoalkyl silane such as N-(2-aminoethyl)-3-aminopropyltrimethoxysilane (AEAP3), (aminoethylaminomethyl)phenethyltrimethoxysilane (AEMP3), or N-(6-aminohexyl)aminopropyltrimethoxysilane (AHAP3)

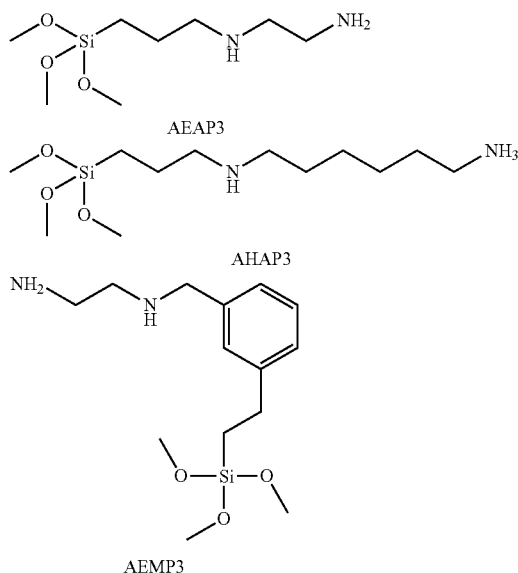

AEMP3

The above formulation is an example of a "polar" sol gel (i.e., a molecule with a dipole moment) and has excellent miscibility characteristics with palladium(II) chloride (5 weight %) in hydrochloric acid (10 weight %). The two can be combined to give a clear, homogeneous solution with very little or no sign of any material precipitation. In contrast, a combination of palladium(II) chloride with a sol gel solution prepared from tetraethyl orthosilicate (TEOS) or octyltriethoxysilane (an example of a "non-polar" sol gel), may lead to a small amount of insoluble material. Radioactive source of palladium, by virtue of its own preparative procedure, can be in the form of palladium(II) chloride in hydrochloric acid.

Further, such "polar" sol gels mixed with palladium can be processed to become a stable xerogel (and/or a sintered gel).

Without wishing to be bound by theory, polar substituent amino groups in "polar" sol gels such as BTMOS/AEAP3 may provide a hydrophilic coordination site for palladium without changing the solubility characteristics of either the palladium compound or sol gel, and without disrupting or disturbing the propagation of the polymer chain as the structure grows. Therefore, the stability and solubility of both the palladium compound and sol gel solution may not be affected, from initial mixing to formation of xerogel. It is noted that palladium has been known to have good affinity for amine-containing compounds such as ammonium chloride and ammonium hydroxide. According to "Sol-Gel Science" (C. J. Brinker and G. W. Scherer, Academic Press, 1990, p. 244), adding a metal salt to a sol could produce an ion exchange:

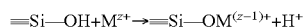

where $M^{z+}$ is an unhydrolyzed cation of charge z. Since the silanol groups provide adsorption sites for water, and such layer of adsorbed water prevents coagulation and is responsible for the stability of the colloid, the removal of SiOH by ion exchange can reduce the amount of hydration and thus destabilizes the aqueous silica sol.

Hence, in the preparation of a relatively "non-polar" sol gel solution using tetraethyl orthosilicate (TEOS) or octyltriethoxysilane, the addition of palladium(II) chloride ($PdCl_2$) most likely causes an ion exchange similar to above. The instability thus results can also affect the solubility of $PdCl_2$ itself, which explains the frequent observation of precipitated material formation. On the other hand, the palladium ion can chelate with the amino groups in a "polar" sol gel and stability may not be affected.

The timing for the addition of $PdCl_2$ has been found to be anywhere between immediately to several days after the preparation of a sol gel solution as demonstrated by the examples below.

Formation of Stable Xerogels from Combination of "Polar" Sol Gel and Pd

A "polar" sol gel solution combined with palladium(II) chloride can be cast onto a surface or substrate and dried to a stable xerogel. Initially, the solvent was allowed to evaporate at room temperature for 2 hours. This time duration may be longer. Without wishing to be bound by theory, it is believed that a "gentle" escape of solvent in a sufficient of amount of time at this low temperature allows the gel to coalesce into a uniform state which is suitable for subsequent temperature ramp-ups in forming a clear stable xerogel. Without this "gentle" evaporation of solvent, adverse effects such as cracking or non-uniform appearance may result. One example of a temperature sequence implemented after this room temperature conditioning has been: a) a gradual increase to 70° C. and holding the temperature there for 1 hour, followed by b) a second increase to 130° C. and holding the temperature there for 2 hours.

This incubation profile generally forms clear, stable xerogel from the "polar" sol gel compositions.

Preparation of a "polar" sol gel may be similar to that published by Marxer, et al. (*Chem. Mater.* 2003, 15, 4193-4199.), the disclosure of which is hereby incorporated by reference in its entirety.

In some embodiments, a sol gel contains a polar substituent such as an amino group, prepared from a mixture of a) a trifunctional alkyl silane and b) a trifunctional aminoalkyl silane, and then combined with a radioactive material, such as palladium metal ions. Such "polar" sol gel can be formed from at least one di- or trifunctional aminoalkyl silane (see below).

The trifunctional alkyl silane can be defined as a silane substituted with a single alkyl and 3 alkoxy groups. The alkoxys are considered functional groups as they take part in the polymerization (hydrolysis and condensation) and are replaced in the process. In other words, the alkoxys may be the reactive sites. The alkyl group, which is generally not a functional group, may be a short-chain carbon unit, e.g., five carbons or less, so as to impart less non-polar characteristics to the resulting polymer. A higher degree of polarity of the sol gel may be desirable for mixing with ionic radioactive sources, such as the ionic palladium compound.

Exemplary trifunctional alkyl silanes are isobutyltrimethoxysilane (BTMOS), isobutyltriethoxysilane, n-butyltrimethoxysilane, n-propyltrimethoxysilane, n-propyltriethoxysilane, n-pentyltriethoxysilane, ethyltrimethoxysilane, ethyltriethoxysilane, and methyltrimethoxysilane.

The trifunctional aminoalkyl silane can be defined as a trialkoxy-substituted silane with a single alkyl substituent, and this alkyl unit contains a single or multiple amino groups. The alkyl substituent may be a shorter chain containing a total of nine carbons or less, or in some embodiments, five carbons or less, and 2 amino groups.

Examples of trifunctional aminoalkyl silanes are N-(2-aminoethyl)-3-aminopropyltrimethoxysilane (AEAP3), (aminoethylaminomethyl)phenethyltrimethoxysilane (AEMP3), N-(6-aminohexyl)aminopropyltrimethoxysilane (AHAP3), N-[3-(trimethoxysily)propyl]diethylenetriamine (DET3) aminopropyltrimethoxysilane, and aminopropyltriethoxysilane.

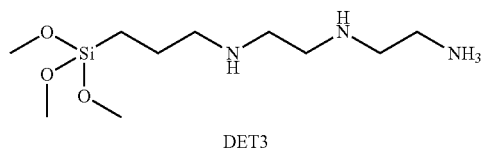 [SMILES: CO[Si](CCCNCCNCCN)(OC)OC]

DET3

In some embodiments, an analogous difunctional diallyl silane can be used in lieu of a trifunctional alkyl silane to provide similar characteristics. Likewise, it is possible that an analogous difunctional di(aminoalkyl) silane or difunctional aminoalkyl alkylsilane can be used in lieu of a trifunctional aminoalkyl silane. The resulting polymeric structure and material and gel characteristics may differ slightly depending on the specific reactants employed to form the sol gel.

It is noted that a "polar" sol gel may be used for incorporating other suitable radioactive sources, including a radioactive palladium or iodine source in basic pH solution. For example, the source material can be palladium (Pd-103) (II) chloride in ammonium hydroxide or other forms of palladium. Other radioactive sources (such as iodine) can also be used and added to the sol gel.

After the sol gel solution is cast onto a surface or substrate, it may be
a) allowed to evaporate at room temperature (25° C.) for 2 hours,
b) heated to 70° C. at a rate of 5° C./min,
c) kept at 70° C. for 1 hour,
d) heated to 130° C. at a rate of 5° C./min, and
e) kept at 130° C. for 2 hours.

To obtain a suitable xerogel formation, one who is skilled in the art can readily modify the temperature incubation profile to suit 1) the polymer structure or characteristics of the sol gel obtained from the selection of a particular trifunctional alkyl silane (or substitute) and a particular trifunctional aminoalkyl silane (or substitute), and 2) a specific material configuration and thickness.

Other Radioactive Materials

Other examples of suitable materials include: 1) Polymerizable materials whose polymerization is initiated by an external stimulus, e.g., laser, UV, heat, or other energy source; 2) Polymerizable materials whose initiation is controlled or regulated. This can be accomplished through the use of microencapsulation technology. Thus, a suitable initiator for polymerization is protected as a microcapsule such that a) the microcapsule wall or layer is dissolved over time, e.g. 4-5 hours, which allows sufficient processing time from initial mixing to filling the fiber holes, or b) the microcapsule wall or layer ruptures upon contact with an external agent when polymerization is called for or when the timing is deemed appropriate, or c) the microcapsule wall or layer ruptures when exposed to an external energy source such as heat or UV.

Accordingly, a line-source and/or a string of radioactive portions along the core can be formed for LDR brachytherapy with increased homogeneity in dose delivery. Flexible materials design can increase biocompatibility, reduce self-shielding effects, and allow for a biodegradable format if desired.

Embodiments according to the present invention will now be described with reference to the following non-limiting examples.

EXAMPLE 1

In one illustrative example according to embodiments of the invention, radioactive Pd-103 in the form of palladium(II) chloride is mixed into a sol gel. The sol can then be dried to form a xerogel. Once the sol-gel based, patterned fiber is completed it can be coated with a biocompatible outer coating and sterilized for clinical use.

The pattern of radioactivity in the device could be determined by the specific requirements for a given patient, e.g., based on brachytherapy planning software. The proper patterning of the radiation pattern in the device can be controlled by a computer configured to translate the clinical brachytherapy prescription into the necessary deposition pattern of radioactivity in the final device.

Small globules (e.g., 5-500 nanoliters) of radioactive sol gel material can be deposited into wells in a micro-patterned suture material. In particular embodiments, the density of globules is about at least 2 globules per 5 mm to about 20 globules per 5 mm or more. In some cases, the globule separations or densities can form a substantially continuous radiation source, i.e., a radiation source with a radiation pattern that is substantially the same as a continuous line source. In other cases the radioactivity along the device can be varied so as to produce a customized, non-uniform radiation pattern.

Once the fiber core is completed, a biocompatible outer coating can be applied by spraying or dip coating or by gluing or heat shrinking a pre-formed tubular material. The biocompatible outer coating could be one of a class of materials used routinely in implantable medical devices (e.g., nylon, polyurethane, silicone, or polyester). The final outer diameter of the coated fiber can ideally be about 0.8 mm so as to be consistent with existing brachytherapy seed products. This can then allow for the device to be placed using the same tools currently in place for LDR prostate brachytherapy. The outer coating can be chosen so that it helps to maintain the desired flexibility of the device so that it may be easily placed through the cannula of an insertion needle and so that it is not subject to breaking or irreversible bending.

EXAMPLE 2

To 9.0 mL isobutyltrimethoxysilane (BTMOS) was added 1.0 mL ethanol, 300 µl water, and 50 µA 0.5 M hydrochloric acid. The mixture was stirred at room temperature for 1 hour. 1.0 mL N-(2-aminoethyl)-3-aminopropyltrimethoxysilane (AEAP3) was then added and stirring was continued for 1 more hour. The resulting solution can be used immediately or stored in a refrigerator for up to 45 days.

In order to add palladium(II) chloride, 0.0137 g of 5 wt. % $PdCl_2$ in 10 wt. % hydrochloric acid (Aldrich) was added to 6.14 mL of the sol gel solution prepared above. This provided a 0.01% Pd (palladium metal) in concentration.

A 2.0 μl aliquot of the prepared sol gel solution containing Pd was applied onto a glass cover slide in a 12 mm circle. It was allowed to evaporate at room temperature for 2 hours uncovered. The material, now a viscous gel film, was then placed inside an oven and the temperature was increased to 70° C. at a rate of 5° C./min. The temperature was maintained at 70° C. for 1 hour, and then increased to 130° C. at a rate of 5° C./min. It was further held at 130° C. for 2 more hours. Upon removal from the oven, a clear, hard xerogel film was obtained. This film showed no or minimal sign of degradation after it was placed in a pH 7.4 buffer solution and heated at 50° C. for 40 hours.

Although embodiments according to the invention have been described with respect to Pd-103, any suitable nuclide for LDR brachytherapy can be used, such as P-32, I-125 and Cs-131.

According to embodiments of the present invention, sol-gel materials can be used for the incorporation of precursor isotopes (subsequently activated) or radioisotopes themselves to form brachytherapy "strings" in the form of elongated source devices. Spatial and/or temporal profiles can be provided by selectively depositing radioactive materials along the length of the device. The sol-gel techniques described herein may be very flexible in terms of what isotopes can be incorporated. In particular embodiments, the metallic isotopes are chemically bound within the sol gel matrix. Various embodiments according to the invention are described herein with regard to implementing LDR brachtherapy device manufacturing.

The sol-gel based string cores can be coated with a biocompatible material (e.g., polyester or nylon), That outer coating may be textured (e.g., with dimples or similar patterns) to enhance the scatter of ultrasonic beams used in imaging. The enhanced scatter allows for easier detection by ultrasound imagers (typically LDR brachytherapy devices are placed under transrectal ultrasound guidance).

As noted above, embodiments of the current invention can be employed in the field of LDR brachytherapy using radioactive isotopes that deliver radiation over an extended period of time from implanted devices. Use of LDR in treating prostate cancer is common. Use of LDR for breast, head & neck, etc. cancers is under development.

The devices described herein may serve as a sealed-source for the containment of the radioisotope(s) as defined by 10 CFR 35.67.

The foregoing is illustrative of the present invention and is not to be construed as limiting thereof. Although a few exemplary embodiments of this invention have been described, those skilled in the art can readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of forming a low-dose-rate (LDR) brachytherapy device, the method comprising:
    providing a substrate having a micropattern thereon, the micropattern including a plurality of spaced-apart wells;
    depositing a radioactive material with a micro-syringe pump and/or micropipette in at least some of the plurality of wells to provide a radiation profile; and
    forming a medical device from the substrate and radioactive material
    wherein depositing the radioactive material comprises depositing a plurality of spaced-apart globules of the radioactive materials having a density of two or more globules per 5 mm and respective volumes for each of the spaced-apart globules of the radioactive material are between 5 and 500 nanoliters.

2. The method of claim 1, wherein the radioactive material is uniformly dispersed at a molecular level.

3. The method of claim 1, wherein the radioactive material comprises one or more of Pd-103, I-125, Cs-131 and P-32.

4. The method of claim 1, further comprising coating the device with a biocompatible coating.

5. The method of claim 1, wherein the spaced-apart globules are adhered to the substrate.

6. The method of claim 1, wherein the substrate comprises an elongated body.

7. The method of claim 6, wherein the elongated body comprises a suture.

8. The method of claim 1, wherein the micro-syringe pump and/or micropipette are controlled by a processor.

9. A method of forming a low-dose-rate (LDR) brachytherapy device, the method comprising:
    providing a substrate having a micropattern thereon, the micropattern including a plurality of spaced-apart wells; and
    depositing a radioactive material in at least some of the plurality of wells to provide a radiation profile, wherein depositing the radioactive material comprises depositing a plurality of spaced-apart globules of the radioactive materials having a density of two or more globules per 5 mm and wherein the density of the spaced-apart globules of radioactive material is 20 or more globules per 5 mm.

10. A method of forming a LDR brachytherapy device, the method comprising:
    determining a radiation profile for the brachytherapy device;
    depositing predetermined volume of a radioactive material in a pattern on the device with a micro-syringe pump and/or micropipette, the radioactive material including a molecularly dispersed radioisotope, the pattern comprising a plurality of spaced-apart, discrete globules, each globule having a respective volume of the radioactive material, the volume of each of the globules being controlled by the micro-syringe pump and/or micropipette, the globules having a density of two or more globules per 5 mm and respective volumes for each of the spaced-apart globules of the radioactive material are between 5 and 500 nanoliters.

11. The method of claim 10, further comprising determining the respective volumes for each of the plurality of globules to provide the radiation profile.

12. The method of claim 10, further comprising determining a distance between each of the plurality of globules to provide the radiation pattern.

13. The method of claim 10, further comprising depositing the respective volumes of the globules so that a deposited volume is within 10% of a predetermined amount.

14. The method of claim 10, further comprising depositing a biocompatible, nondegradable polymeric coating layer on the device.

15. The method of claim 14, further comprising patterning the coating layer to enhance ultrasound visibility.

16. The method of claim 10, wherein depositing the radioactive material comprises depositing the plurality of spaced-apart globules at a density of two or more globules per 5 mm.

17. The method of claim 10, wherein the device is planar.

18. The method of claim 10, wherein the device is an elongated body.

19. The method of claim 10, wherein the device comprises a plurality of microwells, and the radioactive material is deposited in at least some of the microwells.

20. The method of claim 10, wherein the micro-syringe pump and/or micropipette are controlled by a processor.

21. A method of forming a LDR brachytherapy device, the method comprising:

determining a radiation profile for the brachytherapy device;

depositing a radioactive material in a pattern on the device, the radioactive material including a molecularly dispersed radioisotope, the pattern comprising a plurality of spaced-apart, discrete globules, each globule having a respective volume of the radioactive material, wherein respective volumes for each of the globules are between 5 and 500 nanoliters.

22. A method of forming a LDR brachytherapy device, the method comprising:

determining a radiation profile for the brachytherapy device;

depositing a radioactive material in a pattern on the device, the radioactive material including a molecularly dispersed radioisotope, the pattern comprising a plurality of spaced-apart, discrete globules, each globule having a respective volume of the radioactive material, wherein depositing the radioactive material comprises depositing the plurality of spaced-apart globules at a density of 20 or more globules per 5 mm.

\* \* \* \* \*